United States Patent [19]

Boyd et al.

[11] Patent Number: 4,796,632
[45] Date of Patent: Jan. 10, 1989

[54] STANDOFF ADAPTER FOR ULTRASOUND PROBE

[75] Inventors: Ronald J. Boyd, Sacramento; Wing Law, Gold River; Gary L. Wilson, Rancho Cordova, all of Calif.

[73] Assignee: General Electric Company, Milwaukee, Wis.

[21] Appl. No.: 158,087

[22] Filed: Feb. 16, 1988

Related U.S. Application Data

[63] Continuation of Ser. No. 895,342, Aug. 11, 1986, abandoned.

[51] Int. Cl.[4] .............................................. A61B 10/00
[52] U.S. Cl. ................................................ 128/662.03
[58] Field of Search ........................ 128/660, 661, 633; 73/642, 644

[56] References Cited

U.S. PATENT DOCUMENTS

| | | | |
|---|---|---|---|
| 4,059,098 | 11/1977 | Murdock | 73/644 X |
| 4,483,343 | 11/1984 | Beyer et al. | 128/660 |
| 4,579,123 | 4/1986 | Chen et al. | 128/660 |
| 4,603,701 | 8/1986 | Chen | 128/660 |
| 4,671,289 | 6/1987 | Gainsley et al. | 128/660 |

Primary Examiner—Francis J. Jaworski
Attorney, Agent, or Firm—Flehr, Hohbach, Test, Albritton & Herbert

[57] ABSTRACT

An adapter and standoff for an ultrasound probe includes a first compression molded coupler portion and a second compression molded receptacle portion which are assembled to define a fluid cavity for coupling ultrasound waves and a receptacle for receiving a probe head. The coupler portion includes a first housing with a coupling surface on one end thereof and an opening on an opposing end. The receptacle portion includes a second housing with a coupling surface on one end and an opening on an opposing end. The second housing is inserted into the opening of the first housing with the coupling surfaces and the first housing defining the fluid cavity, the opening of the second housing receiving a probe head. The second housing further includes a vent hole for venting air from the fluid cavity and a filler hole for receiving a needle and filling the fluid cavity with a fluid. The receptacle portion includes an adapter ridge which receives a groove in a probe when the probe is fully inserted into the receptacle portion. At least one groove can be provided on an internal surface of the second housing whereby an excess of coupling gel between the probe and the receptacle portion can exit when the probe is fully inserted into the receptacle portion. A tactile feel on an external surface of the second housing aligns with a tactile feel on the probe to ensure proper assembly of the adapter and probe.

11 Claims, 3 Drawing Sheets

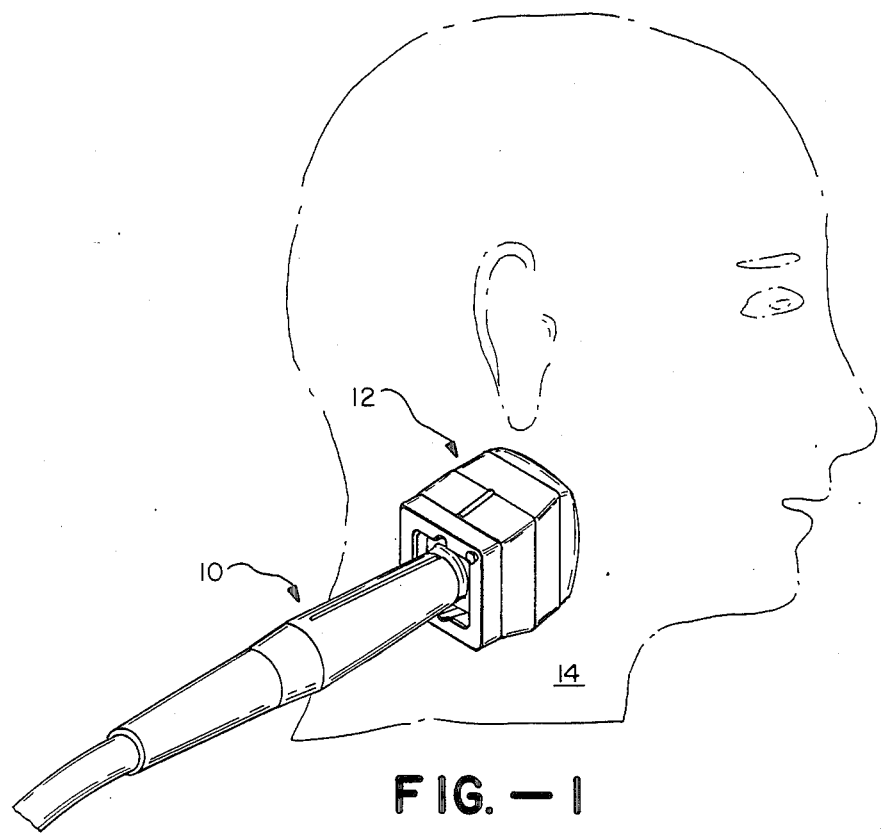
FIG.—1
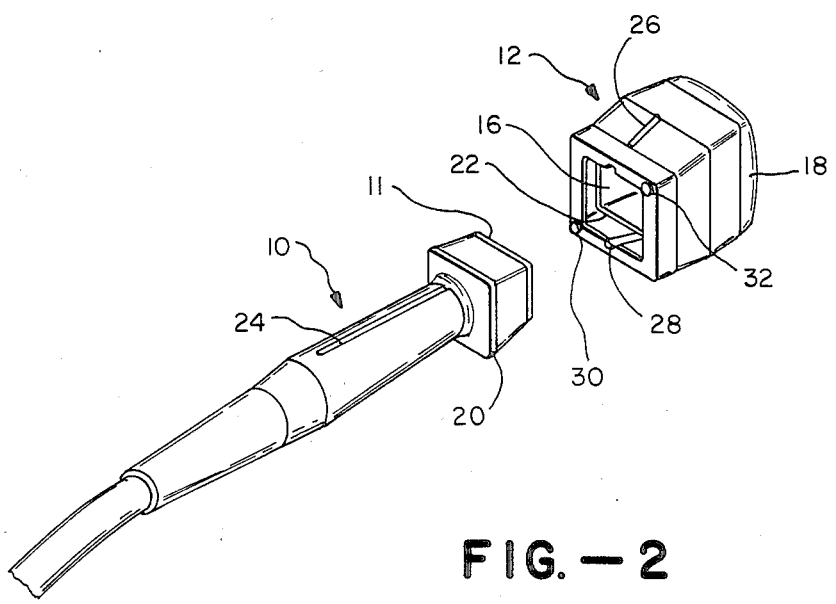
FIG.—2

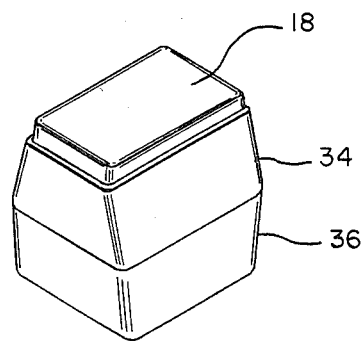
FIG.—7A
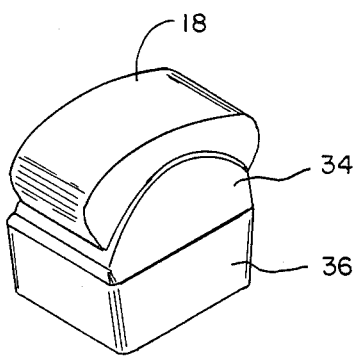
FIG.—7B
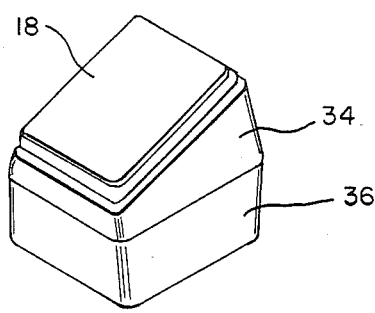
FIG.—7C

STANDOFF ADAPTER FOR ULTRASOUND PROBE

This is a continuation of application Ser. No. 895,342 filed Aug. 11, 1986 and now abandoned.

BACKGROUND OF THE INVENTION

This invention relates generally to ultrasound probes such as used in medical diagnostic imaging systems, and more particularly the invention relates to an adapter for an ultrasound probe which facilitates imaging in the near field of the probe.

Ultrasound systems are now widely used in the medical profession for diagnostic imaging. There exist many systems which employ a phased array transducer probe for transmitting ultrasound signals and receiving reflections thereof from regions of a patient undergoing examination. The signals are steerable continuous or pulsed waves that can be processed to give depth and velocity information. The transmitted signals can be focused to various depths in the patient to be examined. However, a phased array probe has limitations in focus and resolution in the near field that can adversely affect imaging of surface regions such as the carotid artery in the neck, or other small anatomical parts, such as the breast and the testicle.

To provide better near field imaging, previous practices have been to use a material of similar sound velocity as tissue between the probe and the patient as a standoff, the material being 1 to 4 cm in thickness. A commonly accepted clinical practice is to fill a rubber glove with degassed water and place it between the probe and the patient. However, the filled glove tends to be slippery and difficult to position for optimal scanning. Another clinical practice has been to use rubber-like materials as a standoff, such as "fanny fat", which is a silicone gel used normally in floatation pads for supporting patients with superficial burns. The disadvantage of rubber-like materials in general is the high attenuation of soundwave, which limits the penetration in imaging and decreases the signal to noise ratio.

Adapters have been proposed for use with ultrasound transducer probes which can provide a standoff for the probe to facilitate imaging in the near field. One such support is disclosed in U.S. Pat. No. 4,296,753. This support utilizes a series of substantially coaxial, loop shaped elements which are axially arranged one behind the other within a fluid filled coupler. In an alternative embodiment the loop shaped elements are replaced by a spring. The loop shaped elements and spring facilitate the rocking of a probe for varying the direction of imaging. Another ultrasound probe device utilizing a fluid filled support is disclosed in European application No. 84102798, publication No. 0120410. The structure includes a plurality of pieces which are clamped together in a rigid arrangement. Because of the large number of piece parts in these designs, the cost of manufacturing is high. Other manufacturers have used metal or plastic structures to hold a thin plastic or elastomer bagfilled with a coupling material, or used rigid plastics as containers for the coupling fluid with acoustic "windows" made of thin plastic films on the container for the transmission of ultrasound through the container.

The above configurations have sub-optimal image quality when applied to a phased array. A phased array has multiple transmit-receive elements arranged in a regular spacing, similar to an optical grating. The net result of diffraction is the presence of side lobes (grating lobes) at an angle to the main beam. This implies that the transducer will be sensitive not only to objects at the main lobe of the beam, but also to objects at large angles to the beam. Since most rigid objects create strong echoes, the water path standoff consisting of rigid structures tends to increase the clutter in the image. The rigid structures also tend to be uncomfortable to the patient.

SUMMARY OF THE INVENTION

An object of the present invention is an improved standoff adapter for an ultrasound probe that has good image quality and patient comfort.

Another object of the invention is a probe adapter that is economically manufactured.

Still another object of the invention is a probe support that is readily adapted to a probe and is flexible in use.

A feature of the invention is two elastic portions (which may be compression molded) which are joined to form a probe receptacle portion and a fluid filled ultrasound wave coupling portion with sufficient rigidity to hold a shape of optimal acoustic performance without plastic or metal reinforcements.

Another feature of the invention is the provision of filler holes for filling and refilling the fluid cavity.

The invention and objects and features thereof will be more readily apparent from the following detailed description and appended claims when taken with the drawing.

BRIEF DESCRIPTION OF THE DRAWINGS

FIG. 1 is a perspective view of a probe and adapter in accordance with the invention as applied in imaging a patient.

FIG. 2 is an exploded view of the probe and adapter of FIG. 1.

FIGS. 7A-7C are perspective views illustrating other arrangements of the probe adapter in accordance with the invention.

DETAILED DESCRIPTION OF THE ILLUSTRATIVE EMBODIMENTS

Figure 3:
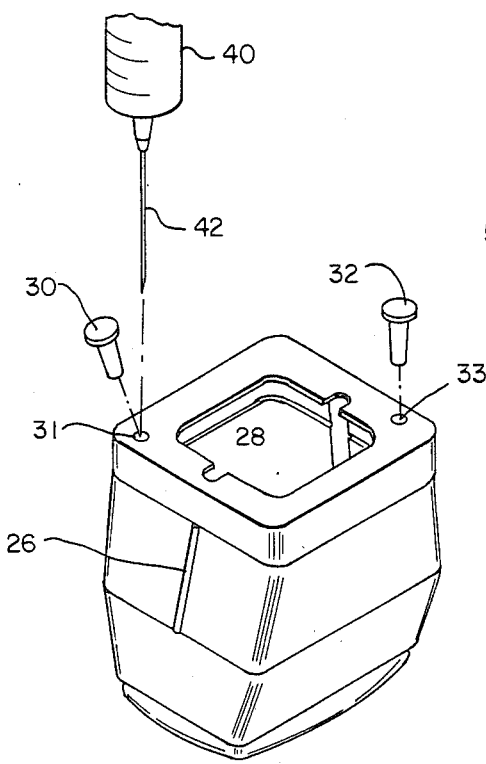
FIG. 3 is a perspective view illustrating the filling of the fluid cavity in the adapter of FIG. 2.

Referring now to the drawings, FIG. 1 is a perspective view illustrating a probe 10 and adapter 12 in accordance with one embodiment of the invention as used in imaging the carotid artery of a patient 14, and FIG. 2 is an exploded perspective view of the probe 10 and adapter 12. The probe 10 utilizes a conventional phased array of transducer elements on an end 11 thereof for transmitting ultrasound waves and receiving reflections thereof from the patient. The standoff adapter 12 in accordance with one embodiment of the invention comprises a structure of compression molded silicone rubber or other suitable and moldable material. The adapter includes a probe receptacle 16 for receiving the head of probe 10 and a coupling surface 18. Between the receptacle 16 and the coupling surface 18 is a fluid filled coupler, as will be described more fully with reference to FIGS. 3-6.

In accordance with one feature of the invention the head of the probe 10 is provided with an undercut groove 20 which mates with an adapter ridge 22 within the receptacle to assure proper alignment of the probe head within the receptacle. Additionally, the probe 10 is provided with tactile feel 24 which is used by the operator for scan image alignment, and the tactile feel 24 aligns with a similar tactile feel 26 on the support 12 to further ensure proper alignment of the probe head in the receptacle 16. To facilitate mating of the probe head in the receptacle 16, a lubricant gel is normally applied to the head and receptacle, and excess lubricant exits through the grooves 28 as the head is inserted into the receptacle. Plugs 30 and 32 are inserted in filler and air exit holes, respectively, for filling the coupler cavity with a suitable ultrasound wave coupling fluid. This is further illustrated in the perspective view of FIG. 3 which illustrates the filling of the coupler cavity with a syringe 40 and needle 42 which is inserted into the hole 31. As fluid is inserted into the coupler cavity, air exits from hole 33. Upon filling of the cavity plugs 30 and 32 are reinserted into holes 31 and 33, respectively.

Figure 4:
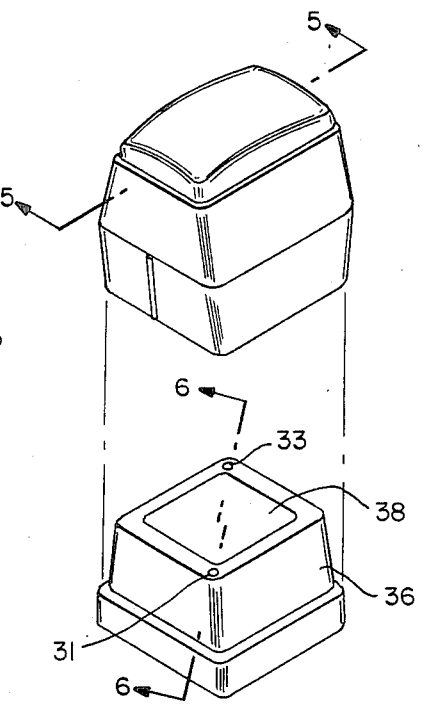
FIG. 4 is an exploded perspective view of the probe adapter illustrating the two mating portions thereof.
Figure 5:
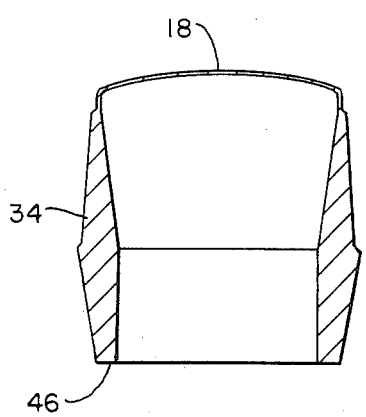
FIG. 5 and 6 are side views in section of the two portions of the support taken along the lines 5—5 and 6—6 in FIG. 4.
Figure 6:
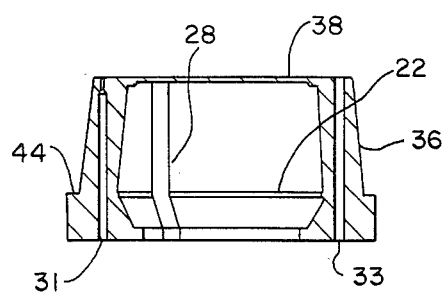

FIG. 4 is an exploded perspective view of the adapter 12 illustrating the two piece construction thereof. The coupler portion 34, further illustrated in section view in FIG. 5 taken along the line 5—5 of FIG. 4, comprises a compression molded housing having a thin coupling surface 18 formed at one end during the compression molding process. The receptacle portion 36 of the support 12 as shown in FIG. 4 and in the section view of FIG. 6 comprises compression molded silicone rubber or other suitable moldable material including a membrane 38 formed during the compression molding of the receptacle housing. When the two portions are assembled, the membranes 18 and 38 cooperate with the housing of the coupler part 34 to define the fluid filled cavity through which ultrasonic waves are coupled. The needle hole 31 and air hole 33 are formed during the compression molding along with the groove 28 and the ridge 22. It will be noted that the bottom of the needle hole 31 is sealed and must be penetrated by the needle during the filling operation. The punctured hole can reseal itself due to the elastic property of the elastomer.

The receptacle portion 36 is assembled in the coupler portion 34 with the flange 44 of the receptacle engaging surface 46 of the coupler portion. The two pieces are fastened together by a suitable adhesive such as silicone RTV.

When the fluid cavity is filled with fluid the two thin membranes 18 and 22 create transparent windows which permit inspection for air bubbles in the cavity. In preferred embodiments the membranes 18 and 38 are on the order of 0.009 inch in thickness.

Since the adapter is made out of an elastomer, in this implementation a silicon rubber, easy insertion of the probe into the adapter is achieved. The adapter is designed to accept and hold the probe tightly in contact with the inner membrane 38. When the probe insertion is complete the mating of the adapter ridge 22 in the groove 20 of the probe can be felt. As above described excess coupling gel between the probe and adapter escapes through the grooves 28.

FIGS. 7A–7C are perspective views illustrating other embodiments of the adapter. In FIG. 7A the configuration is similar to the described embodiment and includes a generally planar coupling surface 18. In FIG. 7B the coupling surface is rounded to facilitate rocking of the probe and adapter for changing the direction of imaging. In FIG. 7C the coupling surface 18 is again generally planar, but the coupler portion 34 of the adapter is inclined to facilitate imaging at an angle with respect to the probe housing. The oblique incidence to the interface between the sound beam and the skin contact eliminates reflections between the probe and the skin contact, which manifests itself as bright echo lines in the image.

The probe adapter in accordance with the invention is low cost and easily attached and detached from the probe. The fluid cavity of the coupler is readily refillable with no special tooling required. Further, clear viewing into the fluid chamber is permitted to observe any bubbles in the cavity or between the probe and the adapter.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. An adapter for an ultrasound probe comprising a first unitary, molded elastic coupler portion and a second unitary, molded elastic receptacle portion, said coupler portion including a first housing with an integral coupling surface on one end of said first housing and an opening on an opposing end of said first housing, said receptacle portion including a second housing with an integral coupling surface on one end of said second housing and an opening on an opposing end of said second housing, said second housing being inserted through said opening of said first housing and nested within said first housing with said coupling surfaces and said first housing defining a fluid cavity for transmitting ultrasound waves and said second housing further including a vent hole for venting air from said fluid cavity and a filler hole for filling said fluid cavity with fluid, said opening of said second housing receiving a probe head whereby said probe head is positioned within said first and second housings and abutting said fluid cavity.

2. The adapter as defined by claim 1 wherein said filler hole is sealed at one end and receives a needle for applying fluid to said fluid cavity.

3. The adapter as defined by claim 2 wherein said receptacle portion includes an adapter ridge within said second housing for receiving a groove in a probe when said probe is fully inserted into said receptacle portion.

4. The adapter as defined by claim 3 wherein said second housing includes at least one groove on an internal surface of said second housing through which a coupling gel between a probe and the receptacle portion can exit when the probe is fully inserted into said receptacle portion.

5. The adapter as defined by claim 4 wherein said second housing has a tactile feel on an external surface thereof for alignment with a probe.

6. The adapter as defined by claim 1 wherein said receptacle portion includes an adapter ridge within said second housing for receiving a groove in a probe when said probe is fully inserted into said receptable portion.

7. The adapter as defined by claim 1 wherein said second housing includes at least one groove on an internal surface thereof whereby excess coupling gel between the probe and said receptacle portion can exit when the probe is fully inserted into said receptacle portion.

8. The adapter as defined by claim 1 wherein said second housing has a tactile feel on an external surface thereof for alignment with a probe.

9. The adapter as defined by claim 1 wherein said coupler portion and said receptacle portion comprise silicone rubber.

10. The adapter as defined by claim 9 wherein said coupler portion and said receptacle portion are bonded together after assembly.

11. The adapter as defined by claim 1 wherein said coupler portion and said receptacle portion comprise compression molded elastomer material.

* * * * *